(12) United States Patent
Fujimoto et al.

(10) Patent No.: US 10,803,290 B2
(45) Date of Patent: Oct. 13, 2020

(54) CLASSIFIER CONSTRUCTION METHOD AND METHOD FOR DETERMINING LIFE OR DEATH OF CELL USING SAME

(71) Applicants: SCREEN HOLDINGS CO., LTD., Kyoto-shi, Kyoto (JP); FRONTIER PHARMA INC., Nagahama-shi, Shiga (JP)

(72) Inventors: Hiroki Fujimoto, Kyoto (JP); Masayoshi Kobayashi, Kyoto (JP); Ryuzo Sasaki, Shiga (JP)

(73) Assignees: SCREEN HOLDINGS CO., LTD., Kyoto (JP); FRONTIER PHARMA INC., Shiga (JP)

( * ) Notice: Subject to any disclaimer, the term of this patent is extended or adjusted under 35 U.S.C. 154(b) by 359 days.

(21) Appl. No.: 15/774,567

(22) PCT Filed: Oct. 26, 2016

(86) PCT No.: PCT/JP2016/081669
§ 371 (c)(1),
(2) Date: May 8, 2018

(87) PCT Pub. No.: WO2017/082048
PCT Pub. Date: May 18, 2017

(65) Prior Publication Data
US 2020/0257886 A1 Aug. 13, 2020

(30) Foreign Application Priority Data

Nov. 10, 2015 (JP) ................................. 2015-220087

(51) Int. Cl.
*G06K 9/00* (2006.01)
*G01N 21/64* (2006.01)
*C12M 1/34* (2006.01)

(52) U.S. Cl.
CPC ......... *G06K 9/00147* (2013.01); *C12M 41/46* (2013.01); *G01N 21/64* (2013.01); *G06K 9/00134* (2013.01)

(58) Field of Classification Search
CPC ........... G06K 9/00147; G06K 9/00134; C12M 41/46; G01N 21/64
(Continued)

(56) References Cited

U.S. PATENT DOCUMENTS

| 7,958,063 | B2* | 6/2011 | Long ................. G06K 9/00147 706/12 |
| 8,260,063 | B2* | 9/2012 | Hasezawa .......... G06K 9/00127 382/225 |

(Continued)

FOREIGN PATENT DOCUMENTS

| JP | 2009-517072 A | 4/2009 |
| JP | 2011-002995 A | 1/2011 |

(Continued)

OTHER PUBLICATIONS

Search Report issued in corresponding International Patent Application No. PCT/JP2016/081669, dated Jan. 24, 2017.
(Continued)

*Primary Examiner* — Jonathan S Lee
(74) *Attorney, Agent, or Firm* — McDermott Will & Emery LLP

(57) ABSTRACT

A technique for automatically and accurately determining life or death of cells in a sample prepared without any labeling, not relying on the subjectivity of a determiner, is intended. A fluorescent specimen in which respective fluorescence generation modes in response to excitation light are different from each other between a living cell and a dead cell is prepared, and fluorescence imaging of the fluorescent specimen is performed. Bright field imaging of the fluorescent specimen is performed, and respective positions of the living cell and the dead cell are specified from a fluorescent image. Image objects in a bright field image, which are located at positions corresponding to the specified positions of the living cell and the dead cell are extracted as a living (Continued)

cell object and a dead cell object, respectively, and a classifier is constructed through machine learning using supervisor data including respective feature vectors of the extracted objects.

6 Claims, 7 Drawing Sheets

(58) Field of Classification Search
USPC .......................................................... 382/133
See application file for complete search history.

(56) References Cited

U.S. PATENT DOCUMENTS

| 2008/0280300 A1 | 11/2008 | Choo |
| 2010/0172555 A1 | 7/2010 | Hasezawa et al. |
| 2011/0294877 A1 | 12/2011 | Masazumi et al. |
| 2015/0131889 A1 | 5/2015 | Aragaki |

FOREIGN PATENT DOCUMENTS

| JP | 2012-506443 A | 3/2012 |
| JP | 2013-203673 A | 10/2013 |
| JP | 2014-029287 A | 2/2014 |
| JP | 2015-521037 A | 7/2015 |
| WO | 2008/129881 A1 | 10/2008 |
| WO | 2013/166336 A1 | 11/2013 |

OTHER PUBLICATIONS

N. Wei et al., "A machine vision system for automated non-invasive assessment of cell viability via dark field microscopy, wavelet feature selection and classification," BMC Bioinformatics, 2008, 9:449, pp. 1-15.

Extended European Search Report issued in corresponding European Patent Application No. 16864012.6, dated Apr. 3, 2019.

M. Tscherepanow, et al., "Automatic Segmentation of Unstained Living Cells in Bright-Field Microscope Images," Advances in Mass Data Analysis of Images and Signals in Medicine, Biotechnology, Chemistry and food Industry, Springer Berlin, Heidelberg, pp. 158-172, 2008.

Xi Long, et al., "Automatic detection of unstained viable cells in bright field images using a support vector machine with an improved training procedure," Computers in Biology and Medicine, Apr. 1, 2006, pp. 339-362.

T. Kurita, "Higher Order Local Autocorrelation Features", Mar. 26, 2019 (Mar. 26, 2019), Retrieved from the Internet: URL:https//home.hiroshima-u.ac.jp/tkurita/papers/fg98parcor/node5.html.

* cited by examiner

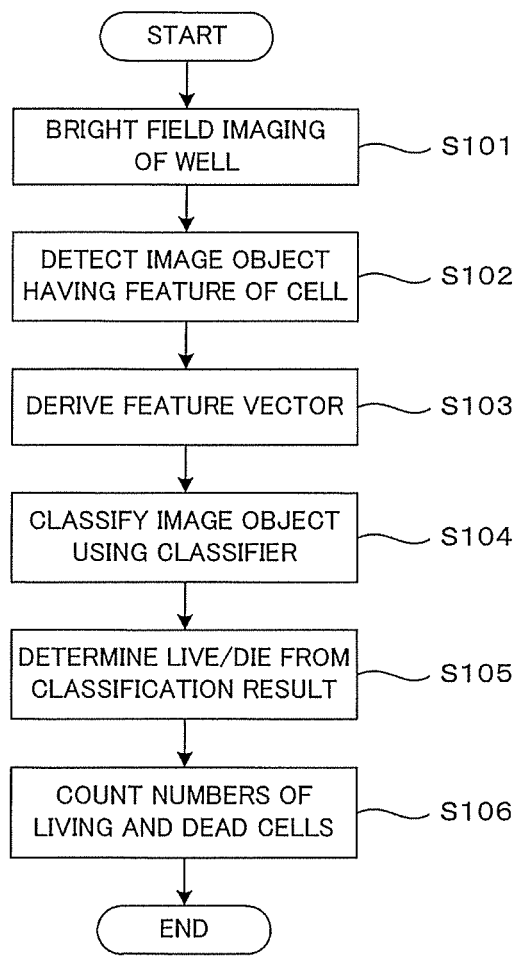

FIG. 7A
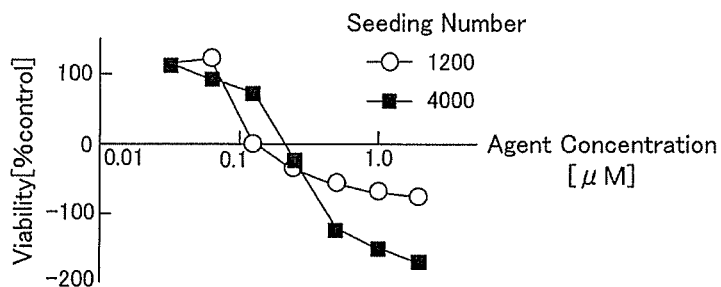
FIG. 7B
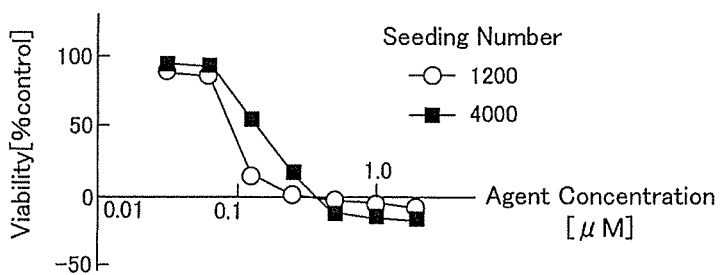
FIG. 7C
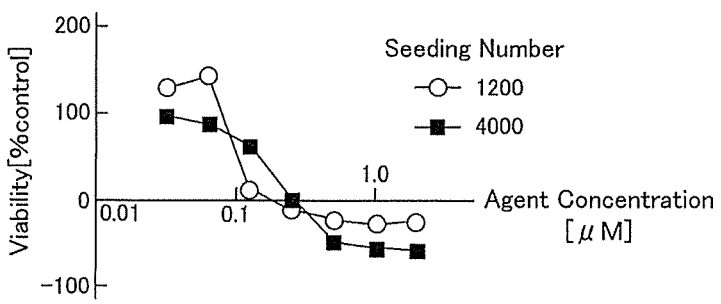
FIG. 7D
| METHOD | ATP ASSAY | | MTT ASSAY | | EMBODIMENT | |
|---|---|---|---|---|---|---|
| Seeding Number | 1200 | 4000 | 1200 | 4000 | 1200 | 4000 |
| IC50[$\mu$M] | 0.0940 | 0.1204 | 0.1026 | 0.1379 | 0.1213 | 0.1561 |
FIG. 7E
| Seeding Number | ATP | MTT |
|---|---|---|
| 1200 | 0.990415 | 0.989925 |
| 4000 | 0.995504 | 0.967863 |

CLASSIFIER CONSTRUCTION METHOD AND METHOD FOR DETERMINING LIFE OR DEATH OF CELL USING SAME

CROSS REFERENCE

This application is the U.S. National Phase under 35 U.S.C. § 371 of International Application No. PCT/JP2016/081669, filed on Oct. 26, 2016, which claims the benefit of Japanese Application No. 2015-220087, filed on Nov. 10, 2015, the entire contents of each are hereby incorporated by reference.

TECHNICAL FIELD

The present invention relates to a technique for determining life or death of a cell on the basis of an image of the cell.

BACKGROUND

For the purpose of drug discovery, for example, a screening experiment is performed in order to study the effects of a compound on cells. In such an experiment, a compound is added, with its concentration changed in various manners, to a sample containing cultured cells, and life or death of the cell is determined at a predetermined timing. Conventionally, such life or death determination of cells has been performed by an expert's visual check using microscopy. In recent years, in order to perform easier and stable determination without relying on the subjectivity of a determiner, a technique for automatically detecting cells and determining life or death thereof, by image analysis using an image in which a sample is imaged, has been developed.

In the technique disclosed in patent literature 1, for example, a sample is stained by using a staining method in which staining can be selectively performed on either live cells (living cells) or dead cells (not living cells), and the stained sample is observed. Thus, the processing in which a label, such as selective coloring in accordance with the type or condition of cells, is given to the cells by performing gene manipulation or reagent addition is referred to as "labeling".

CITATION LIST

[Patent Literature].
[Patent Literature 1] JP2015-521037A

SUMMARY

Technical Problem

In a screening of a compound as a candidate for a medicine, for example, it is necessary to not only check whether the compound effectively acts on a lesion but also confirm that the compound has no ill effect on normal cells. For such a purpose, it is impossible to use labeling which has some effect on cells in a sample. Further, there is a problem that the labeling needs special material and operation and therefore takes high cost and many efforts. For these reasons, establishment of a technique for determining life or death of cells without performing any labeling is required. Any technique for automatically determining life or death of cells with good accuracy from an image without performing any labeling, however, has not been established yet.

Solution to Problem

The present invention is intended to solve the above problem, and it is an object of the present invention to provide a technique for automatically and accurately determining life or death of cells in a sample prepared without performing any labeling, not relying on the subjectivity of a determiner.

One aspect of the present invention is intended for a classifier construction method for determining life or death of a cell, and in order to achieve the above object, the classifier construction method includes a first step for acquiring a fluorescent image obtained by fluorescence imaging of a fluorescent specimen containing a living cell and a dead cell which are different from each other in the fluorescence generation mode in response to excitation light, a second step for acquiring a bright field image obtained by bright field imaging of the fluorescent specimen, a third step for specifying respective positions of the living cell and the dead cell in the fluorescent specimen from the fluorescent image, a fourth step for extracting an image object located at a position in the bright field image corresponding to the position of the living cell specified in the third step, as a living cell object, and extracting an image object located at a position in the bright field image corresponding to the position of the dead cell specified in the third step, as a dead cell object, and a fifth step for obtaining respective feature vectors of the image objects extracted as the living cell object and the dead cell object and constructing a classifier by machine learning using supervisor data including the feature vectors.

The classifier obtained by the invention thus configured makes it possible to automatically determine life or death of cells in a sample prepared without performing any labeling. Specifically, by classification of the images of the cells in the sample, using the classifier constructed by the present invention, it is possible to automatically determine whether the cell more strongly has a characteristic feature of the living cell or the dead cell.

For this purpose, in the present invention, the respective positions of the living cell and the dead cell are specified from the fluorescent image obtained by fluorescence imaging of the fluorescent specimen containing both the living cell and the dead cell. Since the living cell and the dead cell each emit specific fluorescence in the fluorescent image, it is relatively easy to specify the positions in the image. In most cases, however, the shape and texture of the cell is obscure. On the other hand, in the bright field image, though the shape and texture of the cell can be clearly displayed, careful observation is required to distinguish between the living cell and the dead cell from each other.

Then, in the present invention, among the image objects in the bright field image, the image object located at a position corresponding to the position of the living cell in the fluorescent image is extracted as the image object representing the living cell. Further, the image object located at a position corresponding to the position of the dead cell is extracted as the image object representing the dead cell. Thus, the image objects corresponding to the living cell and the dead cell in the bright field image can be specified. By constructing a classifier through machine learning in which feature vectors of these are used as supervisor data, it is possible to obtain a classifier for distinguishing between the living cell and the dead cell from each other on the basis of an image feature. The classifier obtained thus is effective to classify an unknown cell image into either category for the living cell or the dead cell. In other words, by performing classification using this classifier, it is possible to automatically determining life or death of cells with good accuracy, not relying on the subjectivity of a determiner.

Another aspect of the present invention is intended for a method for determining life or death of a cell, which includes a step of acquiring a processing target image obtained by bright field imaging of a sample containing a cell, a step of detecting an image object corresponding to the cell from the processing target image, and a step of classifying the image object which is detected by using the classifier constructed by the classifier construction method as defined in any one of claims 1 through 5 and determining life or death of the cell corresponding to the image object on the basis of a classification result. According to this invention, the image objects in an original image obtained by imaging the sample are classified by using the classifier constructed in the above-described manner. It is therefore possible to automatically determine whether the image object corresponds to the living cell or the dead cell with good accuracy, not relying on the subjectivity of a determiner.

Advantageous Effects of Invention

According to the classifier construction method of the present invention, it is possible to construct a classifier which is useful for automatically and accurately determining life or death of a cell in a sample prepared without performing any labeling. Further, according to the method for determining life or death of a cell in the present invention using the classifier thus constructed, it is possible to automatically and accurately determine life or death of a cell in a sample prepared without performing any labeling.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF DRAWINGS

FIG. 3 is a flowchart showing a cell counting process in the imaging apparatus.

FIG. 7A is a first view showing a result of comparison between a determination method of the embodiment and already-existing determination methods.

FIG. 7B is a second view showing a result of comparison between a determination method of the embodiment and already-existing determination methods.

FIG. 7C is a third view showing a result of comparison between a determination method of the embodiment and already-existing determination methods.

FIG. 7D is a fourth view showing a result of comparison between a determination method of the embodiment and already-existing determination methods.

FIG. 7E is a fifth view showing a result of comparison between a determination method of the embodiment and already-existing determination methods.

DESCRIPTION OF EMBODIMENTS

Figure 1:
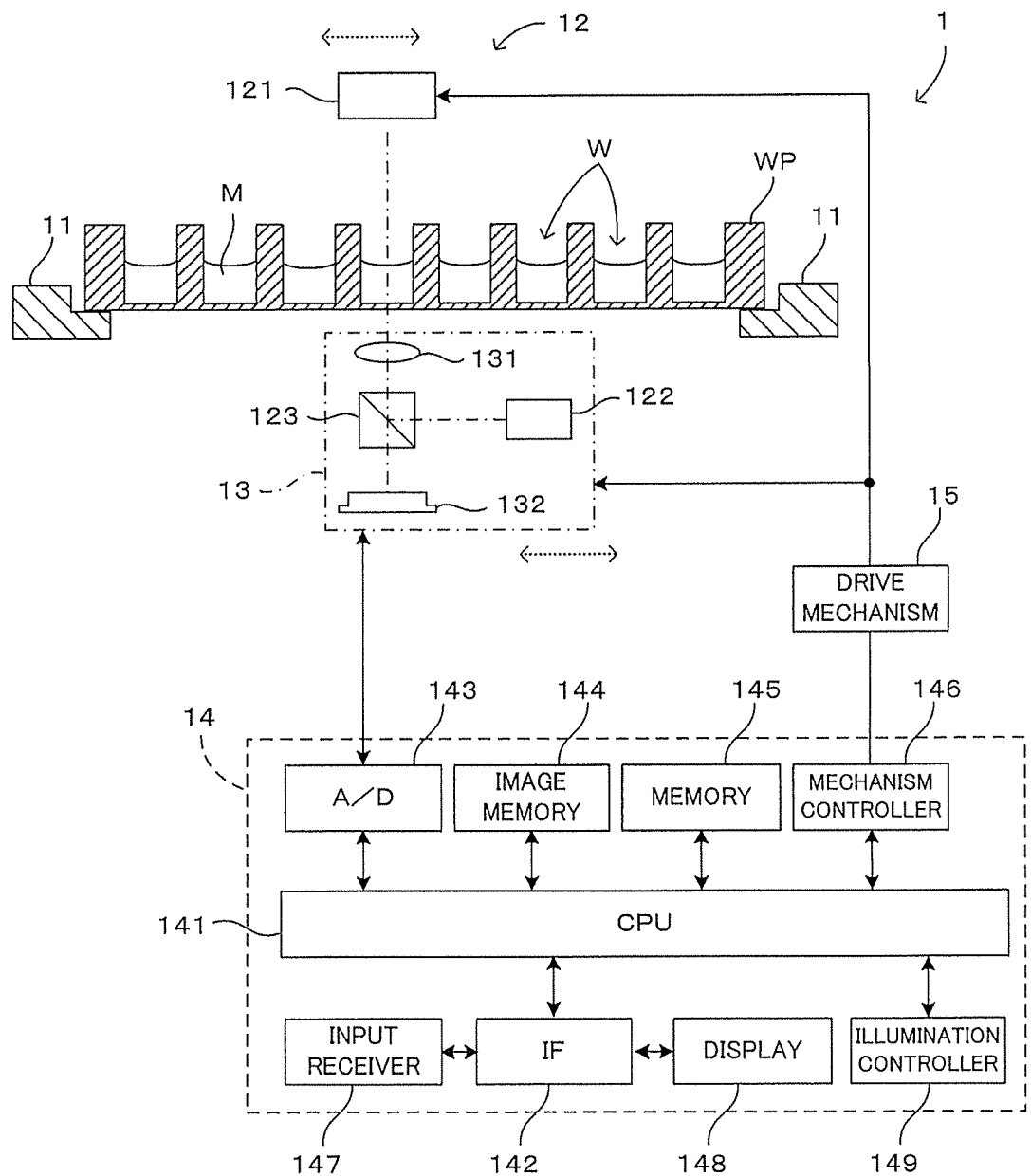
FIG. 1 is a diagram showing a schematic configuration of an imaging apparatus to which the present invention can be applied.

FIG. 1 is a diagram showing a schematic configuration of an imaging apparatus to which the present invention can be applied. This imaging apparatus 1 is an apparatus for imaging a cell or cell colony cultured in liquid poured into recesses called wells W formed on the upper surface of a well plate WP. An up and down direction in FIG. 1 indicates a vertical direction and the down direction is a vertically down direction. A right and left direction in FIG. 1 and the direction perpendicular to a face of FIG. 1 indicate a horizontal direction.

The well plate WP is generally used in the fields of drug discovery and bioscience. A plurality of wells W having a substantially circular cross-section and a transparent and flat bottom surface are disposed to the upper surface of a plate having a flat plate shape. The number of the wells W on the well plate WP is arbitrary. For example, a well plate WP having 96 (12×8 matrix array) wells can be used. A diameter and a depth of each well W are typically about several mm. Note that the size of a well plate and the number of wells used in this imaging apparatus 1 are arbitrary without being limited to these. For example, well plate having 6 through 384 wells may be used. Further, the imaging apparatus 1 can be applied to image the cell or the like not only in the well plate provided with a multitude of wells but also, in a flat container called a dish, for example.

A predetermined amount of liquid as a culture medium M is poured into each well of the well plate WP. A cell or the like cultured under predetermined culture conditions in this liquid is an imaging object of this imaging apparatus 1. The culture medium M may be added with appropriate reagents or may be gelled after being poured into the wells W in a liquid state. In this imaging apparatus 1, for example, a cell or the like cultured on an inner bottom surface of the well can be an imaging object as described later. The liquid amount depends on specifications of the plate. About 100 to 200 microliters to the 96 wells and about 25 to 75 microliters to the 384 wells are generally usually used, for example.

The imaging apparatus 1 includes a holder 11 which holds the well plate WP, an illuminator 12 arranged above the holder 11, an imager 13 arranged below the holder 11 and a controller 14 which includes a CPU 141 controlling the operation of these components. The holder 11 holds the well plate WP in a substantially horizontal posture by being held in contact with a peripheral edge part of the lower surface of the well plate WP carrying sample together with liquid in each well W.

The imager 13 is provided below the well plate WP held by the holder 11. In the imager 13, an imaging optical system is arranged at a position right below the well plate WP. An optical axis of the imaging optical system extends in a vertical direction.

The imaging of the cell or the like in the well W is performed by the imager 13. Specifically, light emitted from the illuminator 12 and incident on the surface of the liquid from above the well W illuminates the imaging object. Light transmitted downward from the bottom surface of the well W is incident to a light receiving surface of an imaging element 132 via the imaging optical system including an objective lens 131. An image of the imaging object is formed on the light receiving surface of the imaging element 132 by the imaging optical system is imaged by the imaging element 132. The imaging element 132 is a linear image sensor having a one-dimensional light receiving surface or an area image sensor having a two-dimensional light receiving surface. A CCD sensor or a CMOS sensor can be used as the imaging element 132. Note that as the imaging element 132, an imaging element capable of color imaging is used.

The illuminator 12 includes a first light source 121 disposed above the well plate WP and a second light source 122 disposed below the well plate WP. The first light source 121 has, for example, a white LED (Light Emitting Diode) as an illumination light source, and emits downward white light as visible illuminating light for lighting the cells in the well W. On the other hand, the second light source 122 has a fluorescence excitation light source, and emits intense monochromatic light in a substantially horizontal direction on the side of the bottom surface of the well plate WP. A wavelength of the light emitted from the second light source 122 is selected in accordance with a fluorescent reagent to be used. For example, when GFP (Green Fluorescent Protein) and PI (Propidium Iodide) described later are observed at the same time, blue light having a wavelength of 470 nm can be preferably used.

The illuminator 12 also includes a fluorescence mirror unit 123 disposed below the well plate WP. The fluorescence mirror unit 123 is disposed substantially at the same position as the position of the first light source 121 in a horizontal direction and substantially at the same position as the position of the second light source 122 in a vertical direction. The second light source 122 and the fluorescence mirror unit 123 in the illuminator 12 are accommodated in the same case as the imager 13 is accommodated in. Then, the fluorescence mirror unit 123 is disposed between the imaging optical system and the imaging element 132 in the imager 13. As described below, the light emitted selectively from the first light source 121 or the second light source 122 enters the fluorescence mirror unit 123. The fluorescence mirror unit is, for example, a dichroic mirror.

Figure 2A:
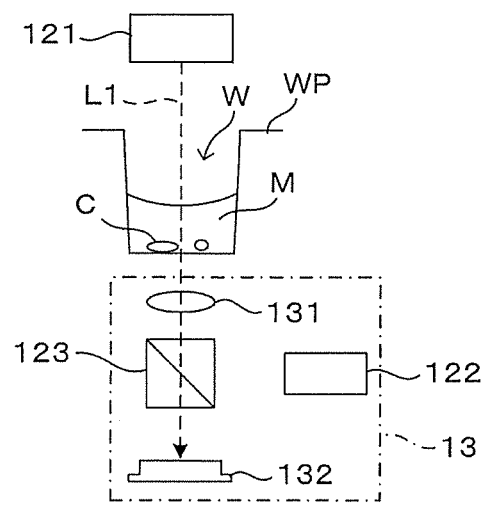
FIG. 2A is a first diagram showing an operation of the illuminator.
Figure 2B:
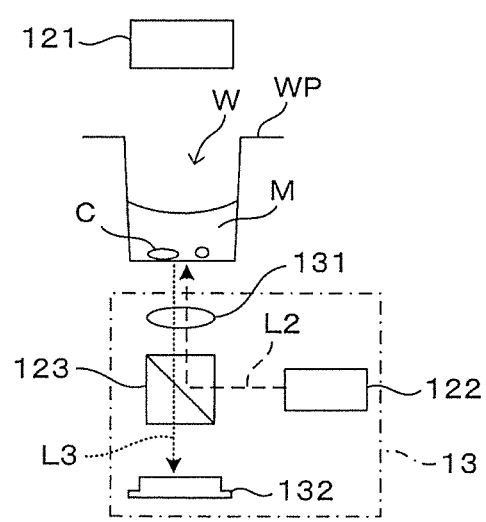
FIG. 2B is a second diagram showing an operation of the illuminator.

FIGS. 2A and 2B are diagrams each showing an operation of the illuminator. In more detail, FIG. 2A is an optical path diagram of the light emitted from the first light source 121. FIG. 2B is an optical path diagram of the light emitted from the second light source 122. As shown in FIG. 2A, light L1 emitted downward from the first light source 121 enters the culture medium M in the well W from upward and performs bright field illumination on a cell C in the culture medium M, which is an imaging target. The light L1 is emitted downward from the transparent bottom surface of the well W and enters the fluorescence mirror unit 123 through the objective lens 131. The fluorescence mirror unit 123 transmits the light L1 downward and causes the light L1 to enter the imaging element 132 disposed therebelow.

On the other hand, as shown in FIG. 2B, excitation light L2 having a relatively short wavelength, which is emitted from the second light source 122, is reflected upward on the fluorescence mirror unit 123 and enters the cell C in the culture medium M through the objective lens 131 and the bottom surface of the well W. As described later, when the cell C is given a property of generating fluorescence by the excitation light, fluorescence is generated from the cell C by the excitation light L2. The fluorescence L3 having a wavelength longer than that of the excitation light, which is emitted from the cell C, passes through the objective lens 131 and the fluorescence mirror unit 123 and enters the imaging element 132. Thus, the first light source 121 and the second light source 122 which selectively emit light, together with the fluorescence mirror unit 123, constitute an illumination optical system which achieves coaxial illumination on the cell C.

In a state where the illumination light L1 is emitted from the first light source 121 in the illuminator 12 onto the well W, the image imaged by the imager 13 is a bright field image of the well W. On the other hand, in a state where the excitation light L2 is emitted from the second light source 122 onto the well W, the image imaged by the imager 13 is a fluorescent image of the well W, which is obtained by capturing the image of the fluorescence L3 excited by the excitation light L2. The excitation light L2 does not directly enter the imaging element 132. The positional relation between the well W and the imager 13 is not changed in both imagings and the imaging visual field is the same as each other.

The imager 13 is capable of moving in the horizontal direction and the vertical direction by a mechanism controller 146 provided in the controller 14. Specifically, the mechanism controller 146 operates a drive mechanism 15 based on a control command from the CPU 141. The drive mechanism 15 moves the imager 13 in the horizontal direction, thereby the imager 13 moves relative to the well W in the horizontal direction. Further, focusing is performed by moving the imager 13 in the vertical direction.

Further, the as indicated by arrows with dotted lines shown in FIG. 1, the driving mechanism 15 moves the illuminator 12 (the first light source 121, the second light source 122 and the fluorescence mirror unit 123) integrally with the imager 13 when the imager 13 is moved in the horizontal direction. Specifically, the illuminator 12 is arranged such that a center of emitted light substantially coincides with the optical axis of the imager 13. When the imager 13 moves in the horizontal direction, the illuminator 12 also moves in conjunction with the imager 13.

When an image of one well W in detail is required, the imaging is performed in a state that a whole of the well W is included in a field of view. In this time, the mechanism controller 146 positions the imager 13 in the horizontal direction such that the optical axis of the imaging optical system coincides with the center of the well W. By doing so, whichever well W is imaged, the center of the well W and the center of emitted light are always position on the optical axis of the imaging optical system. Consequently, the illuminating condition becomes constant regardless of which well W is to be imaged, wherefore imaging conditions can be maintained to be satisfactory.

On the other hand, when imaging is required to perform with a plurality of the wells W more quickly, the imaging is performed with moving the imager 13 horizontally. Specifically, the mechanism controller 146 realizes a scan movement by moving the illuminator 12 and the imager 13 integrally with constant speed in the horizontal direction. The imager 13 performs imaging periodically, thereby a wider area is imaged. Particularly, when the imaging device of the imager 13 is the one-dimensional image sensor, a two-dimensional image can be obtained by the scan movement of the imager 13 relative to the imaging object.

The image signal output from the imaging element 132 of the imager 13 is send to the controller 14. Specifically, the image signal is input to an AD converter (A/D) 143 provided in the controller 14 and converted into digital image data. The CPU 141 performs appropriate image processings based on the received image data. The controller 14 further includes an image memory 144 for storing image data and a memory 145 for storing programs to be executed by the CPU 141 and data generated by the CPU 141, but these may be integrated. The CPU 141 performs variable calculation processings described later by executing a control program stored in the memory 145.

Besides, the controller 14 is provided with an interface (I/F) 142. The interface 142 has a function of performing data exchange with an external apparatus connected via a communication line besides a function of receiving an operation input from a user and presenting information such as processing results to the user. To realize the user interface function, an input receiver 147 for receiving an operation input from the user and a display 148 for displaying the messages to the user, a processing result or the like are connected to the interface 142. Further, the controller 14 includes an illumination controller 149 which controls lighting of the first light source 121 and the second light source 122.

Note that the controller 14 may be an exclusive device including above hardware or may be a general-purpose processing device such as a personal computer or a workstation installed with the control program for performing the process described later. Specifically, a general-purpose computer apparatus may be used as the controller 14 of the imaging apparatus 1. When a general-purpose processing device is used as the controller 14, the imaging apparatus 1 may have just a minimal control function for controlling each components of the imager 13.

The imaging apparatus 1 having the above constitution has the function of determining life or death of cells cultured in the well W from an image acquired by imaging of the inside of the well W, and counting the number of determined living cells and that of determined dead cells. Hereinafter, an operation of the imaging apparatus 1 will be described. The operation described below is implemented when the CPU 141 executes a control program stored in advance in the memory 145 and causes each of the constituent elements of the apparatus to perform a predetermined operation defined in the control program.

FIG. 3 is a flowchart showing a cell counting process in the imaging apparatus. Though counting the number of cells is performed individually for each of a plurality of wells W provided in the well plate WP, description will be made herein, paying attention to an operation on one well W. First, in a state where the illumination light L1 is emitted from the first light source 121 of the illuminator 12 onto the well W, bright field imaging of the inside of the well W is performed by the imager 13 (Step S101). A bright field image of the well W is thereby obtained. Imaging may be performed individually on each of the wells W or may be performed collectively on the plurality of wells W.

The following processing is performed individually on each of the wells W. With an imaged image of one well W and the inside thereof as a processing target image, an image object having the form of a cell is detected from the inside of the well W in the processing target image (Step S102). To the detection of the image object, various well-known techniques may be applied. For example, a method in which an area where pixels having pixel values larger (or smaller) than a threshold value determined as appropriate continuously exist is extracted may be applied. For setting the threshold value, for example, an adaptive threshold method in which a threshold value is dynamically set in accordance with the brightness of the background may be used. An image object which is considered apparently not to represent a cell from the shape thereof may be excluded.

Next, a plurality of types of feature amounts representing morphological characteristics of the detected image objects by numerical values are obtained and feature vectors in which these feature amounts serve as elements are obtained (Step S103). By using the feature vectors obtained thus and a classifier based on an appropriate classification algorithm created in advance by a method described later, the image objects are classified (Step S104). This classifier has the function of classifying the image objects into one of a plurality of classification categories including a "living cell" category and a "dead cell" category on the basis of the feature vectors. Further, since the detected image objects may include an image object representing a cell which is unclear on whether it is living or dead or another image object representing something that is not a cell (such as bubble), some classification categories corresponding to these image objects may be prepared.

The viability (living or dead) of the cell is determined on the basis of the classification result (Step S105). Specifically, among the detected image objects, the image object classified into the "living cell" category is determined as a living cell. Further, the image object classified into the "dead cell" category is determined as a dead cell. Thus, after whether each cell is living or dead is determined, the number of image objects determined as the living cell and that of image objects determined as the dead cell are counted (Step S106).

Next, a method of constructing the classifier used for the above-described determination process will be described. In order to construct the classifier on the basis of an appropriate learning algorithm and classify life or death of a cell, image samples serving as typical examples of the living cell and the dead cell are needed. Such image samples can be prepared on the basis of the determination through expert's visual check. For the purpose of collecting the typical examples, however, many image samples without any wrong determination are needed, and it is not realistic to perform the operation relying on the visual check determination. Hereinafter, specific examples of collection of the typical examples not relying on any visual check determination and of the classifier construction method through machine learning using the collected typical examples as supervisors will be described.

Figure 4:
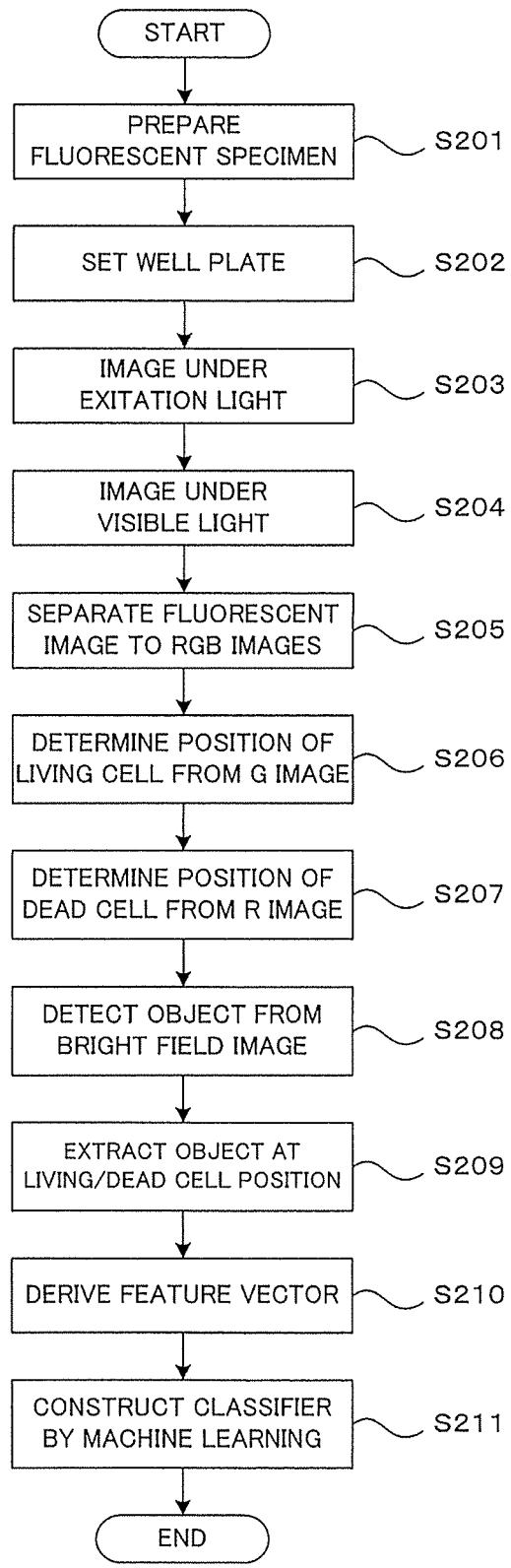
FIG. 4 is a flowchart showing the classifier construction method in the embodiment.

FIG. 4 is a flowchart showing the classifier construction method in the embodiment. First, fluorescent specimens for acquiring image samples in a case of using GFP (corresponding to the living cell) and PI stain (corresponding to the dead cell) are prepared (Step S201). As the fluorescent specimens, the same type of cells as the cells which are targets for determination of life or death thereof, to which labels representing different fluorescence generation modes in response to the excitation light in accordance with whether the cells are living or dead are given, are used. The specimens need to include both the living cell and the dead cell. Here, a method of creating the specimens including both the living cell and the dead cell will be described. However, both the living cell and the dead cell do not need to be included in one specimen, but a specimen mainly including the living cell and another specimen mainly including the dead cell may be individually prepared.

In this embodiment, a cell which develops a green fluorescent protein (GFP) as a fluorescent protein for example and has been grown in the well W of the well plate WP is used. The fluorescent specimen is obtained by adding a predetermined chemical agent to the cell and after a predetermined period elapses, adding thereto, for example, propidium iodide (PI) as a fluorescent dye. The GFP emits green fluorescence in response to the excitation light having a short wavelength if the cell incorporating the GFP therein is living. On the other hand, the PI, which is used as a dead cell staining reagent, emits red fluorescence in response to the excitation light by combining with the DNA of the dead cell.

In the fluorescent specimen in which part of cells are killed by adding the chemical agent, the living cells and the dead cells are mixed. When blue light having a wavelength of 470 nm, for example as the excitation light, is allowed to be incident to this fluorescent specimen, the living cell emits the green fluorescence caused by the GFP and the dead cell emits the red fluorescence caused by the PI respectively. Then, the living cell and the dead cell can be clearly distinguished in the fluorescent image.

The well plate WP in which the fluorescent specimen is created is set in the imaging apparatus 1 (Step S202). Then, the imager 13 images an image under the emission of the excitation light from the second light source 122, and the fluorescent image is acquired (Step S203). Further, the imager 13 images an image under the emission of the illumination light from the first light source 121, and the bright field image is acquired (Step S204). The order of imagings of the fluorescent image and the bright field image may be arbitrary, but it is preferable that the time interval between these imagings should be short in order to avoid any movement or state change of the cell. In the configuration of the present embodiment in which the excitation light and the illumination light are selectively emitted by the coaxial illumination optical system, it is possible to sufficiently shorten this time interval.

In order to distinguish between a green component caused by the GFP and a red component caused by the PI, the fluorescent image is captured as a color image. The acquired fluorescent image is separated by the RGB color component (Step S205). On the other hand, as to the bright field image, though a color image is required in a case where the feature amount relating to color is used in a post-processing, otherwise color information can rather complicate the processing. In such a case, in order to make it unnecessary to perform the processing for each color, even when the image is captured as a color image, it is preferable to monochromatize the color image by appropriate image processing.

Figure 5:
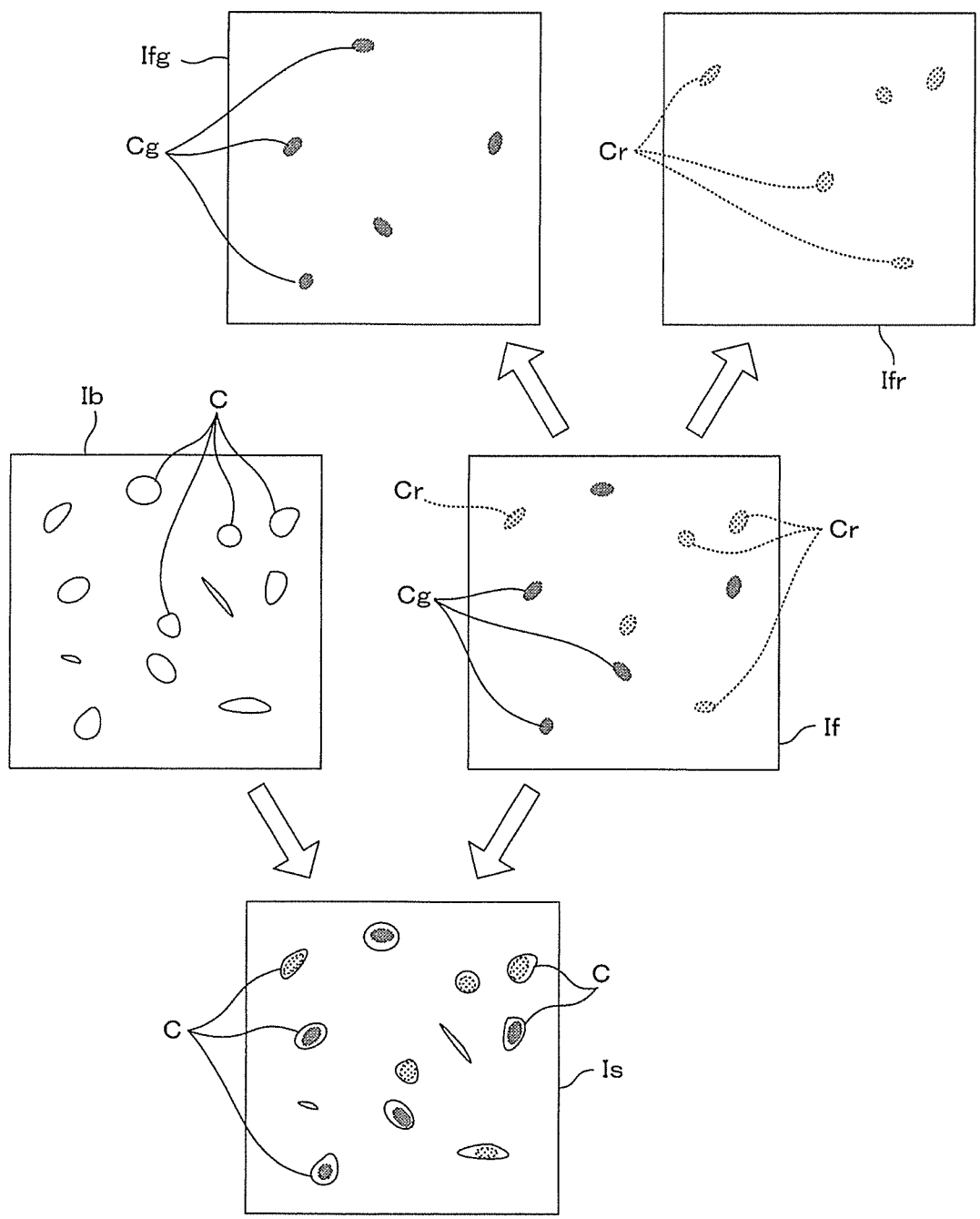
FIG. 5 is a view showing examples of the imaged image and various images derived therefrom.

FIG. 5 is a view showing examples of the imaged image and various images derived therefrom. In the bright field image Ib, though the shape and contour of the cell C are shown relatively sharply, it is necessary to observe each cell C in detail in order to determine life or death of the cell. On the other hand, in the fluorescent image If, a green image Cg caused by the GFP appears at the position of the living cell and a red image Cr caused by the PI appears at the position of the dead cell. Therefore, in a G (green) single-color image Ifg obtained by separating the fluorescent image If, the image Cg appears at the position of the living cell, and in an R (red) single-color image Ifr, the image Cr appears at the position of the dead cell respectively. Further, depending on the fluorescent dye used herein, each of the RGB color components can have a component value. Even in this case, by using a known method for color image processing, it is possible to specify an area having the color.

Thus, in the fluorescent image If, the living cell and the dead cell are distinguished by the color of fluorescence and the positions of these cells are clearly represented. Detailed information on the shape of the cell, however, is lost. Herein, if the bright field image Ib and the fluorescent image If are overlapped, in a composite image Is, whether each cell C appearing in the bright field image is living or dead is indicated by the fluorescent color. By using this principle, it is possible to distinguish the cells C in the bright field image into the living cells and the dead cells.

With reference back to FIG. 4, description of the method of constructing the classifier will continue. From the G single-color image and the R single-color image obtained by separating the fluorescent image, respective positions of the living cell and the dead cell are specified (Steps S206 and 207). In the G single-color image obtained by separating the fluorescent image, an image object corresponding to the fluorescence caused by the GFP appears. Therefore, by binarizing the image with an appropriate threshold value set with respect to a luminance value of the G color component, for example, the distribution of the objects corresponding to the living cells in the image can be seen. The position of the living cell can be represented by, for example, the centroid position of each object in the binary image. Similarly, as to the R single-color image, by binarizing the image, the position of an object corresponding to the fluorescence caused by the PI is specified. Thus, the respective positions of the living cells and the dead cells in the fluorescent image are specified.

Next, an image object included in the bright field image is detected (Step S208). Detection of the image object can be performed by using an appropriate one of known detection methods. For example, the adaptive threshold method described above and various segmentation methods can be used. The image object detected thus can include the living cells, the dead cells, and the objects which are not the living cells or dead cells.

Out of the image objects in the bright field image, which are detected thus, image objects located at the positions corresponding to the positions of the living cells and the positions of the dead cells in the fluorescent image are extracted (Step S209). The bright field image and the fluorescent image are imaged by the same imager 13 in the same imaging visual field. As shown in FIG. 5, when the bright field image Ib and the fluorescent image If are overlapped, the image objects corresponding to the living cells or the dead cells among the image objects in the bright field image Ib overlap the image objects in the fluorescent image If.

From this point, it is estimated with high probability that among the image objects in the bright field image Ib, the image object including the centroid position of the living cell detected in the fluorescent image If corresponds to the living cell and the image object including the centroid position of the dead cell in the fluorescent image If corresponds to the dead cell. Hereinafter, the image object estimated as the living cell is sometimes referred to as a "living cell object". Similarly, the image object estimated as the dead cell is sometimes referred to as a "dead cell object". The living cell object can be used as a typical example of the image of the living cell, and the dead cell object can be used as a typical example of the image of the dead cell. Among the image objects in the bright field image, the image object corresponding to bubble or the like which is not the living cell or the dead cell can be distinguishably considered as an extraneous matter that is not a cell since there is no image object corresponding thereto in the fluorescent image.

For each of the image object corresponding to the living cell and that corresponding to the dead cell which are extracted thus, the feature vector is obtained (Step S210). By performing a machine learning algorithm with an appropriate supervisor using the label indicating whether each object is the living cell or the dead cell and the feature vector as supervisor data, the classifier is constructed (Step S211). The constructed classifier includes a "living cell" category and a "dead cell" category as the classification category and has the function of classifying unclassified image objects into any one of these categories. The classifier constructed thus is used in the cell counting process (Step S105) shown in FIG. 3.

It is preferable to provide a classification category such as a "non-cell" for the image object, among the image objects in the bright field image Ib, which does not correspond to the living cell or the dead cell and in other words, does not correspond to any object in the fluorescent image If. Specifically, the feature vector is derived also for such an image object (Step S210) and used as the supervisor data. By performing the classification, in the determination process shown in FIG. 3, the image object not representing a cell is classified into the non-cell, and it is possible to avoid wrong determination on whether such an object is the living cell or the dead cell. The image objects not representing any cell may be further classified into a plurality of classification categories.

These classification categories in the classifier may be prepared in advance prior to the execution of the machine learning. Further, an expert may give the classification categories ex post facto for clusters which are automatically formed by using a self-organizing learning algorithm.

As to the feature amount serving as an element of the feature vector, well-known feature amounts which quantitatively represent the morphological characteristics appearing in a cell in a visible image can be appropriately selected. From the findings of the inventor of the present application, for the purpose of determining life or death of the cells, a contour feature amount representing the external-shape characteristics of the cell and a texture feature amount representing the texture inside the cell are effective and the combination of these feature amounts can produce a better effect. As the contour feature amount, for example, a normal angle histogram in which directions indicated by the normals of the contour of the object are obtained for each pixel on the contour and statistically processed can be used. Further, as the texture feature amount, for example, a high-order local auto-correlation (HLAC) on the inside of the cell surrounded by the contour is used.

Figure 6:
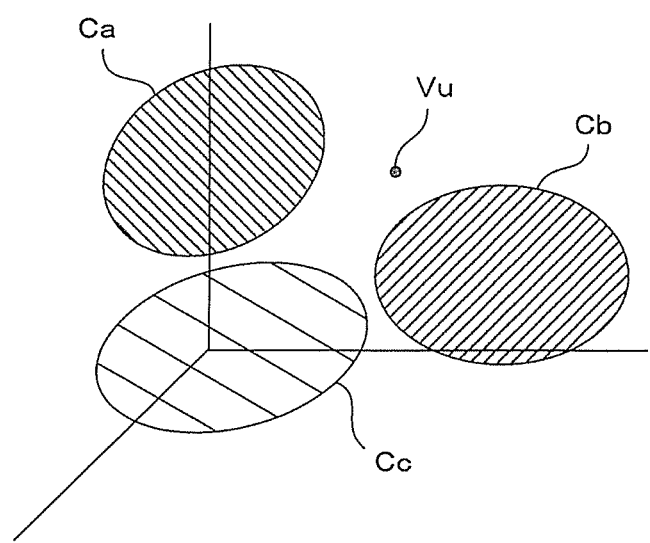
FIG. 6 is a graph illustrating clusters formed by the learning in a feature space.

FIG. 6 is a graph illustrating clusters formed by the learning in a feature space. The image objects extracted from the bright field image are mapped with respect to one point specified by the feature vector in the feature space constituted of a plurality of feature amount axes. The image objects are clustered for each classification category in the feature space by the machine learning based on the supervisor data.

FIG. 6 schematically shows one example, herein illustrating three clusters, i.e., a cluster Ca corresponding to the "living cell" category, a cluster Cb corresponding to the "dead cell" category, and a cluster Cc corresponding to the "non-cell" category. A feature vector Vu corresponding to the unclassified image object is classified into the classification category corresponding to one cluster having the shortest distance in the feature space among these clusters. Thus, as to the unknown image object extracted from the bright field image, it is determined whether the unknown image object corresponds to a cell or not, and when the image object corresponds to the cell, it is further determined whether the cell is living or dead.

FIGS. 7A to 7E are views showing a result of comparison between a determination method of the embodiment and already-existing determination methods. In order to evaluate the accuracy of life or death determination of cells in the embodiment, the inventor of the present application performed a comparative experiment between the method of the embodiment and the ATP assay and the MTT assay which are already-existing life or death determination methods and have achieved a certain degree of results in the determination accuracy. Specifically, a sample obtained by causing the chemical agent MG132 as an anticancer agent to act on a NIH3T3 cell cancerated by introducing Ras gene thereto was prepared. Then, the viability of the cell and the 50% inhibitory concentration (IC50) after a predetermined time elapsed are measured in each of the ATP assay, the MTT assay, and the embodiment, and the respective measurement results were compared.

The respective values of viability measured while changing the combination of the seeding number of cells and the diluted concentration of the chemical agent in various manners are shown in FIGS. 7A to 7C. FIG. 7A shows a result of the ATP assay, FIG. 7B shows that of the MTT assay, and FIG. 7C shows that of the embodiment. The numerical values of viability obtained by using the already-existing ATP assay and MIT assay are each represented as the ratio of the "quantity" of living cells to the total cells in the sample.

On the other hand, in the embodiment, since the number of living cells and that of dead cells can be individually counted, the numerical value of viability was obtained by the following method. First, in each of the sample in which the chemical agent is added and the sample in which no chemical agent is added, the count value of living cells immediately before giving the chemical agent is subtracted from that of all the living cells. Then, the value of ratio obtained by dividing the number of living cells in the sample in which the chemical agent is added by the number of living cells in the sample in which no chemical agent is added and representing by the percentage was adopted as the value of viability. It can be found from FIGS. 7A to 7C that the substantially same measurement results were obtained by three types of methods.

From these graphs, a value of IC50 is obtained. Specifically, by performing fitting using a sigmoid function from a plurality of data points sandwiching 50% therebetween in values of the viability, a chemical agent concentration having a viability value of 50% is obtained and the value of the concentration is determined as the IC50. When numerical values are compared with each other and one of the values falls within the range from 0.5 times to twice the other value, it can be regarded that sufficient correlation is taken between these values. As shown in FIG. 7D, extremely close numerical values are acquired in the determination methods. The degrees of correlation in the value of the IC50 between the determination method of the embodiment and the ATP assay and the MTT assay are shown in FIG. 7E. It can be seen that extremely high correlation is achieved between these already-existing determination methods and the determination method of the present embodiment.

Thus, in this embodiment, in order to construct the classifier which distinguishes between the living cell and the dead cell from the image objects included in the bright field image, a correspondence relation in the image objects between the fluorescent image and the bright field image in the fluorescent specimen subjected to labeling in advance is used. Specifically, the fluorescent specimen is created so that the living cell and the dead cell may emit different fluorescences in the fluorescent image, and from the fluorescent image obtained by imaging the fluorescent specimen, the respective positions of the living cell and the dead cell are specified.

Then, among the image objects detected in the bright field image, an image object located at the position where the living cell is detected in the fluorescent image is regarded as the image object corresponding to the living cell (living cell object). On the other hand, an image object located at the position where the dead cell is detected is regarded as the image object corresponding to the dead cell (dead cell object). These image objects are used as the typical examples of the living cell and the dead cell respectively, and the classifier is constructed through supervised machine learning using these feature vectors.

As to the unclassified image object detected in the image obtained by imaging the sample including a cell which is a target for determination of life or death, by performing classification using the classifier constructed as above, it is possible to determine life or death on the basis of the feature vectors derivable from the appearance of the object in the bright field image. Therefore, once the classifier is completed, it is not necessary to label in advance on an unknown sample and it is possible to avoid any effect produced on cells in the sample by the procedure for labeling. Further, it is possible to reduce the cost and efforts required for the labeling operation. Particularly, it is very helpful to eliminate the necessity of the labeling in the screening experiment which needs to evaluate a large amount of samples.

Further, the learning in constructing the classifier is performed with the image objects on which life or death is obviously determined by association with the fluorescent image, as the typical examples. For this reason, no expert's determination is needed and it is possible to acquire a stable determination result, not relying on the subjectivity of a determiner.

As described above, in the classifier construction method of the above-described embodiment (FIG. 4), Steps S203, S204, S206 to S207, S208 to S209, and S210 to S211 correspond to a "first step", a "second step", a "third step", a "fourth step", and a "fifth step" of the present invention, respectively. Further, in the imaging apparatus 1 of the above-described embodiment, the imager 13 serves as an "imager" of the present invention.

Further, in the cell counting process (FIG. 3) of the above-described embodiment, Steps S101, S102, and S103 to S105 correspond to a "step of acquiring a processing target image", a "step of detecting an image object", and a "step of determining life or death" of the present invention, respectively. Then, the processing of Steps S101 to S105 as a whole corresponds to a "life or death determination method" of the present invention.

Note that the invention is not limited to the above embodiment and various modifications other than those described above can be made without departing from the scope of the invention. For example, the labeling method for the fluorescent specimen and the selection of the feature amounts in the above-described embodiment are each just one exemplary case and not restrictive.

Further, the imaging apparatus 1 of the above embodiment includes both the function of imaging the fluorescent specimen prepared in advance and constructing the classifier and the function of imaging the unknown sample and determining life or death of the cell. However, the process of acquiring an image of the fluorescent specimen, the process of constructing the classifier by using the image, the process of imaging an image of the unknown sample, and the process of determining life or death of the cell from the image are independent from one another. Therefore, it is not always necessary to perform all the processes by a single-unit apparatus. For example, the processes of imaging the fluorescent specimen and constructing the classifier and the processes of imaging the unknown sample and determining life or death of the cell may be performed by different apparatuses.

An apparatus for imaging the fluorescent specimen and the sample and another apparatus for constructing the classifier and determining life or death on the unknown sample by using the acquired images may be separately provided. Further, the difference in the appearance characteristics between the living cell and the dead cell depends on the type of cell and the type of chemical agent, not depending on the constitution of the apparatus for imaging these fluorescent specimen and sample and the content of the image processing. Therefore, when a plurality of environments for determining life or death of a cell are provided, for example, the classifier for the cell, which is prepared by the above-described method, can be used commonly to these plurality of environments. In these cases, the configuration for performing fluorescence imaging is not needed in the imaging apparatus for imaging the unknown sample.

In the imaging apparatus 1 of the above embodiment, the excitation light source for fluorescence imaging and the illumination light source for bright field imaging make coaxial illumination, and these imagings are performed by the same imager 13 in the same imaging visual field. However, so long as the fluorescence imaging and the bright field imaging for the same specimen are performed at a short time interval and the positional relation in the images is clear between the fluorescent image and the bright field image, the fluorescence imaging and the bright field imaging may be performed in different environments.

Thus, as has been described with the specific embodiment illustrated, in the present invention, for example, there may be a configuration where the imager images an image of the fluorescent specimen irradiated with the excitation light which excites the fluorescence in the first step, and the same imager as in the first step images an image of the fluorescent specimen irradiated with a visible light as the illumination light in the same imaging visual field as in the first step in the second step. In such a configuration, it is not necessary to move the fluorescent specimen between the fluorescence imaging and the bright field imaging and it is possible to avoid any change in the state of the cell between these imagings. Further, since an image of the same cell appears at the same position between the fluorescent image and the bright field image, the positional relation therebetween is extremely clear.

Further, for example, the fluorescent specimen may be made by adding a red fluorescent dye as a dead cell staining reagent to cells which are introduced with a green fluorescent protein and cultured. At that time, there may be a configuration where a color image of the fluorescent specimen is acquired in the first step and an area having a predetermined luminance or more in a green single-color image obtained by separating the color image is determined as the living cell and an area having a predetermined luminance or more in a red single-color image obtained by separating the color image is determined as the dead cell in the third step.

In such a configuration, an image object appears only at the position of the living cell in the G single-color image and an image object appears only at the position of the dead cell in the R single-color image. For this reason, the respective positions of the living cell and the dead cell can be easily and reliably specified. Further, since an image object representing something that is not a cell can be excluded, it is possible to avoid wrong determination and increase the accuracy of the classifier constructed thus.

Furthermore, for example, the feature vector may include at least one of the contour feature amount relating to the shape of the contour of the image object and the texture feature amount relating to the texture inside the image object, as an element. In this case, the texture feature amount may include a feature amount relating to, for example, the high-order local auto-correlation. From the findings of the inventor of the present application, these feature amounts can be preferably used for the purpose of determining life or death of a cell with good accuracy.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

INDUSTRIAL APPLICABILITY

The present invention can be preferably applied to the purpose of objectively and quantitatively evaluating the viability of a cell. For example, the present invention can be used to quantitatively evaluate medical efficacy of a compound acting on a cell for the purpose of drug discovery screening. Further, for example, the present invention can be preferably used to evaluate the validity of a regenerative medicine technology using a pluripotent stem cell such as the iPS cell, the ES cell, or the like.

REFERENCE SIGNS LIST 1 imaging apparatus
13 imager (imager)
C cell
Ib bright field image
If fluorescent image
S101 step of acquiring a processing target image
S102 step of detecting an image object
S103 to S105 step of determining life or death
S203 1st step
S204 2nd step
S206 to S207 3rd step
S208 to S209 4th step
S210 to S211 5th step

The invention claimed is:

1. A classifier construction method for determining life or death of a cell, the classifier construction method comprising:
 a first step for acquiring a fluorescent image obtained by fluorescence imaging of a fluorescent specimen containing a living cell and a dead cell which are different from each other in the fluorescence generation mode in response to excitation light;
 a second step for acquiring a bright field image obtained by bright field imaging of the fluorescent specimen;
 a third step for specifying respective positions of the living cell and the dead cell in the fluorescent specimen from the fluorescent image;
 a fourth step for extracting an image object located at a position in the bright field image corresponding to the position of the living cell specified in the third step as a living cell object, and extracting an image object located at a position in the bright field image corresponding to the position of the dead cell specified in the third step as a dead cell object; and
 a fifth step for obtaining respective feature vectors of the image objects extracted as the living cell object and the dead cell object and constructing a classifier by machine learning using supervisor data including the feature vectors.

2. The classifier construction method according to claim 1, wherein in the first step, an imager images the fluorescent specimen irradiated with the excitation light which excites the fluorescence, and in the second step, the imager same as in the first step images the fluorescent specimen irradiated with a visible light as an illumination light in a same imaging visual field as in the first step.

3. The classifier construction method according to claim 1, wherein the fluorescent specimen is made by adding a red fluorescent dye as a dead cell staining reagent to cells which are introduced with a green fluorescent protein and cultured,
 in the first step, a color image of the fluorescent specimen is acquired, and
 in the third step, an area having a predetermined luminance or more in a green single-color image obtained by separating the color image is determined as the living cell and an area having a predetermined luminance or more in a red single-color image obtained by separating the color image is determined as the dead cell.

4. The classifier construction method according to claim 1, wherein the feature vector includes at least one of a contour feature amount relating to a shape of a contour of the image object and a texture feature amount relating to a texture inside the image object as an element.

5. The classifier construction method according to claim 4, wherein the texture feature amount includes a feature amount relating to a high-order local auto-correlation.

6. A method for determining life or death of a cell, comprising:
 a step of acquiring a processing target image obtained by bright field imaging of a sample containing a cell;
 a step of detecting an image object corresponding to the cell from the processing target image; and
 a step of classifying the image object by using the classifier constructed by the classifier construction method according to claim 1 and determining life or death of the cell corresponding to the image object on a basis of a classification result.

* * * * *